United States Patent
Phillip et al.

(10) Patent No.: US 10,342,827 B2
(45) Date of Patent: Jul. 9, 2019

(54) NUTRITIONAL SUPPLEMENT FOR GROWTH ENHANCEMENT

(71) Applicant: NG Solutions LTD., Petach-Tikva (IL)

(72) Inventors: Moshe Phillip, Givataim (IL); Michal Yackobovitch-Gavan, Netanya (IL); Raanan Shamir, New York, NY (US); Hadassa Bymel, Haifa (IL); Liora Lazar, Tel-Aviv (IL)

(73) Assignee: NG Solutions LTD, Petach-Tikva (IL)

( * ) Notice: Subject to any disclaimer, the term of this patent is extended or adjusted under 35 U.S.C. 154(b) by 0 days.

(21) Appl. No.: 14/774,869

(22) PCT Filed: Jan. 29, 2014

(86) PCT No.: PCT/IL2014/050098
§ 371 (c)(1),
(2) Date: Sep. 11, 2015

(87) PCT Pub. No.: WO2014/155373
PCT Pub. Date: Oct. 2, 2014

(65) Prior Publication Data
US 2016/0022734 A1     Jan. 28, 2016

Related U.S. Application Data

(60) Provisional application No. 61/805,747, filed on Mar. 27, 2013, provisional application No. 61/862,533, filed on Aug. 6, 2013.

(51) Int. Cl.
| | | |
|---|---|---|
| A61K 33/30 | (2006.01) | |
| A61K 31/198 | (2006.01) | |
| A61K 33/06 | (2006.01) | |
| A61K 31/375 | (2006.01) | |
| A61K 33/26 | (2006.01) | |
| A61K 31/07 | (2006.01) | |
| A61K 31/592 | (2006.01) | |
| A61K 31/593 | (2006.01) | |
| A61K 31/70 | (2006.01) | |
| A61K 38/16 | (2006.01) | |
| A23L 33/15 | (2016.01) | |
| A23L 33/155 | (2016.01) | |
| A23L 33/16 | (2016.01) | |
| A23L 33/17 | (2016.01) | |

(52) U.S. Cl.
CPC ............ *A61K 33/30* (2013.01); *A23L 33/15* (2016.08); *A23L 33/155* (2016.08); *A23L 33/16* (2016.08); *A23L 33/17* (2016.08); *A61K 31/07* (2013.01); *A61K 31/198* (2013.01); *A61K 31/375* (2013.01); *A61K 31/592* (2013.01); *A61K 31/593* (2013.01); *A61K 31/70* (2013.01); *A61K 33/06* (2013.01); *A61K 33/26* (2013.01); *A61K 38/16* (2013.01); *A23V 2002/00* (2013.01)

(58) Field of Classification Search
CPC ..................................................... A61K 31/07
See application file for complete search history.

(56) References Cited

U.S. PATENT DOCUMENTS

| | | | | |
|---|---|---|---|---|
| 5,922,766 A | * | 7/1999 | Acosta | A23L 1/296 426/601 |
| 6,346,264 B1 | | 2/2002 | White | |
| 6,352,713 B1 | * | 3/2002 | Kirschner | A23L 1/302 424/439 |
| 8,287,932 B2 | | 10/2012 | Rosales | |
| 2006/0024408 A1 | | 2/2006 | Cicci | |
| 2006/0088574 A1 | * | 4/2006 | Manning | A23L 1/296 424/439 |
| 2007/0037861 A1 | | 2/2007 | Cutfield | |
| 2007/0243290 A1 | * | 10/2007 | Thompson | A23L 1/293 426/72 |
| 2010/0136134 A1 | * | 6/2010 | Boehm | A23L 1/296 514/1.1 |
| 2010/0266723 A1 | | 10/2010 | Bralley, III | |
| 2013/0017182 A1 | | 1/2013 | Lukina | |
| 2018/0140632 A1 | | 5/2018 | Phillip et al. | |

FOREIGN PATENT DOCUMENTS

| | | |
|---|---|---|
| CN | 101048167 | 10/2007 |
| CN | 103096735 | 5/2013 |
| WO | 2011/149713 A1 | 12/2011 |
| WO | WO2012/089783 | * 12/2011 |
| WO | WO 2014/155373 | 10/2014 |

OTHER PUBLICATIONS

Abrams et al., (2003) A multinutrient-fortified beverage enhances the nutritional status of children in Botswana. J Nutr 133(6): 1834-40.
Alarcon et al., (2003) Effect of oral supplementation on catch-up growth in picky eaters. Clin Pediatr (Phila) 42(3): 209-17.
Allen (1994) Nutritional influences on linear growth: a general review. Eur J Clin Nutr 48 Suppl 1: S75-89.
Allen et al., (1992) The interactive effects of dietary quality on the growth and attained size of young Mexican children. Am. J Clin Nutr 56(2): 353-64
Beckett et al., (2000) Effects of an energy and micronutrient supplement on anthropometry in undernourished children in Indonesia. Eur J Clin Nutr 54 Suppl 2: S52-9.
Bhandari et al., (2001) Effect of micronutrient supplementation on linear growth of children. Br J Nutr 85 Suppl 2: S131-7.
Boonstra et al., (2006) Food intake of children with short stature born small for gestational age before and during a randomized GH trial. Horm Res 65(1): 23-30.

(Continued)

*Primary Examiner* — Adam C Milligan
*Assistant Examiner* — Sarah Alawadi

(57) ABSTRACT

Provided are nutritional supplements designed for enhancing the growth, particularly the linear growth, of pre-pubertal children with a stature measure short compared to the norm. The nutritional composition includes an energy source, arginine and a combination of micronutrients.

4 Claims, No Drawings

(56) References Cited

OTHER PUBLICATIONS

Brown et al., (2002) Effect of supplemental zinc on the growth and serum zinc concentrations of prepubertal children: a meta-analysis of randomized controlled trials. Am J Clin Nutr 75(6): 1062-71.
Cohen et al., (2008) Consensus statement on the diagnosis and treatment of children with idiopathic short stature: a summary of the Growth Hormone Research Society, the Lawson Wilkins Pediatric Endocrine Society, and the European Society for Paediatric Endocrinology Workshop. J Clin Endocrinol Metab 93(11): 4210-7.
Cole and Lifshitz (2008) Zinc nutrition and growth retardation. Pediatr Endocrinol Rev 5(4): 889-96.
Fahmida et al., (2007) Zinc-iron, but not zinc-alone supplementation, increased linear growth of stunted infants with low haemoglobin. Asia Pac J Clin Nutr 16(2): 301-9.
Fawzi et al., (1997) Dietary vitamin A intake in relation to child growth. Epidemiology 8(4): 402-7.
Fuchs et al., (1994) Relationship between vitamin A deficiency, malnutrition, and conjunctival impression cytology. Am J Clin Nutr 60(2): 293-8.
Gibson et al., (2007) Does zinc deficiency play a role in stunting among primary school children in NE Thailand? Br J Nutr 97(1): 167-75.
Hakimi et al., (2006) The effect of supplemental zinc on the height and weight percentiles of children. Arch Iran Med 9(2): 148-52.
Imamoğlu et al., (2005) Effect of zinc supplementation on growth hormone secretion, IGF-I, IGFBP-3, somatomedin generation, alkaline phosphatase, osteocalcin and growth in prepubertal children with idiopathic short stature. J Pediatr Endocrinol Metab 18(1): 69-74.
Isidori et al., (1981) A study of growth hormone release in man after oral administration of amino acids. Curr Med Res Opin 7(7): 475-81.
Kuczmarski et al., (2000) CDC growth charts: United States. Adv Data (314): 1-27.
Kurugöl et al., (2000) Vitamin A deficiency in healthy children aged 6-59 months in Izmir Province of Turkey. Paediatr Perinat Epidemiol 14(1): 64-9.
Lawless et al., (1994) Iron supplementation improves appetite and growth in anemic Kenyan primary school children. J Nutr 124(5): 645-54.
Lebenthal et al., (2014) Effect of a nutritional supplement on growth in short and lean prepubertal children: a prospective, randomized, double-blind, placebo-controlled study. J Pediatr 165(6): 1190-1193. e1.
Owen et al., (1971) Preschool children in the United States: who has iron deficiency? J Pediatr 79(4): 563-8.
Perrone et al., (1999) Long-term zinc and iron supplementation in children of short stature: effect of growth and on trace element content in tissues. J Trace Elem Med Biol 13(1-2): 51-6.
Ramakrishnan et al., (2004) Multimicronutrient interventions but not vitamin a or iron interventions alone improve child growth: results of 3 meta-analyses. J Nutr 134(10): 2592-602.
Rao et al., (1980) Association of growth status and the prevalence of anaemia in preschool children. Indian J Med Res 71: 237-46.
Rosado (1999) Separate and joint effects of micronutrient deficiencies on linear growth. J Nutr 129(2S Suppl): 531S-533S.
Rosado et al., (1997) Zinc supplementation reduced morbidity, but neither zinc nor iron supplementation affected growth or body composition of Mexican preschoolers. Am J Clin Nutr 65(1): 13-9.
Sachdev et al., (2006) Effect of iron supplementation on physical growth in children: systematic review of randomised controlled trials. Public Health Nutr 9(7): 904-20.
Sguassero et al., (2012) Community-based supplementary feeding for promoting the growth of children under five years of age in low and middle income countries. Cochrane Database Syst Rev 6: CD005039.
Thibault et al., (1993) Idiopathic prepubertal short stature is associated with low body mass index. Horm Res 40(4): 136-40.
Wudy et al., (2005) Children with idiopathic short stature are poor eaters and have decreased body mass index. Pediatrics 116(1): e52-7.
Zadik et al., (2010) "Functional food" for acceleration of growth in short children born small for gestational age. J Pediatr Endocrinol Metab 23(5): 435-41.
Pediasure® retrieved on Aug. 4, 2015 (URL: http://www.abbottnutrition.ca/en/docs.NutriGuidesPDF/12568_PNPG_EN.pdf).
Allen et al., (2009) Provision of multiple rather than two or fewer micronutrients more effectively improves growth and other outcomes in micronutrient-deficient children and adults. J Nutr 139(5): 1022-1030.
International Preliminary Report on Patentability dated Sep. 29, 2015 From the International Searching Authority Re. Application No. PCT/IL2014/050098. (6 Pages).
International Search Report and the Written Opinion dated May 19, 2014 From the International Searching Authority Re. Application No. PCT/IL2014/050098. (8 Pages).
Notification of Office Action dated Oct. 11, 2016 From the State Intellectual Property Office of the People's Republic of China Re. Application No. 201480018435.7 and Its Translation Into English. (14 Pages).
Supplementary European Search Report and the European Search Opinion dated Nov. 4, 2016 From the European Patent Office Re. Application No. 14773050.1. (5 Pages).
Abbott "Abbott Nutrition for Health Care Professionals", Product Information, 2 P., 2016.
Notification of Office Action and Search Report dated Jul. 4, 2017 From the State Intellectual Property Office of the People's Republic of China Re. Application No. 201480018435.7. (11 Pages).
Translation of Notification of Office Action dated Jul. 4, 2017 From the State Intellectual Property Office of the People's Republic of China Re. Application No. 201480018435.7. (16 Pages).
Refusal of Patent dated Jun. 6, 2018 From the National Intellectual Property Office of Sri Lanka Re. Application No. 4-18429. (1 Page).
Savendahl "The Effect of Acute and Chronic Stress on Growth", Presentation of the European Society for Paediatric Endocrinology (ESPE), New Inroads to Child Health (NICHe) Conference on Stress Responses and Child Health, Heraklion, Crete, Greece, May 18-20, 2012, Science Signaling, 5(247): Pt.9, p. 1-14, Oct. 23, 2012.
Examination Report dated Apr. 10, 2018 From the Australian Government, IP Australia Re. Application No. 2014240730. (5 Pages).
Official Action dated May 11, 2018 From the US Patent and Trademark Office Re. U.S. Appl. No. 15/876,340. (21 Pages).
WebHealthCentre "Height / Weight Charts for Children", WebHealthCare, 2 P., 2015.
Examination Report dated Aug. 14, 2018 From the Australian Government, IP Australia Re. Application No. 2014240730. (4 Pages).
Office Action dated Oct. 14, 2018 From the Israel Patent Office Re. Application No. 241469 and Its Translation Into English. (6 Pages).
Examination Report dated Jan. 12, 2019 From the National Intellectual Property Office of Sri Lanka Re. Application No. 4-18429. (2 Pages).
Official Action dated Nov. 30, 2018 From the US Patent and Trademark Office Re. U.S. Appl. No. 15/876,340. (30 pages).

* cited by examiner

NUTRITIONAL SUPPLEMENT FOR GROWTH ENHANCEMENT

FIELD OF THE INVENTION

The present invention relates to the field of nutritional supplements, particularly to a nutritional supplement comprising an energy source together with standardized amounts of micronutrients including arginine effective in enhancing the growth of short and lean pre-pubertal children.

BACKGROUND OF THE INVENTION

Growth is the fundamental physiologic process that characterizes childhood, and adequate nutrition is essential for normal growth. In a rapidly growing child, there is an increased need for "building materials" for the newly synthesized tissues.

Height as a growth parameter is measured as a linear stature at a single point in time compared to expected norms. The norms are typically provided by the general population as depicted in growth charts consisting of a series of percentile curves that illustrate the distribution of selected body measurements in children (for example, the charts of the Centers for Disease Control and Prevention (CDC)). Growth can be worrisome along two variables: height (short stature) and velocity (growth failure).

The American Academy of Pediatrics defines short stature based on height as more than two standard deviations below the average height of the population. A child with short stature is shorter than approximately 97.5% of children of a similar age and gender and typically attains final adult heights of no more than approximately 5'4" (about 162.5 cm) for boys and 4'11" (about 150 cm) for girls.

The major cause of growth retardation worldwide is poverty related malnutrition; when suboptimal nutrition is continued for prolonged periods of time, growth stunting occurs as the main clinical phenotype.

Micronutrients are nutrients required only in minute amounts by the human body, but nevertheless play a critical role in the normal growth and development of the body. Deficiencies in micronutrients can lead to a breakdown in numerous bodily functions and result in a plethora of mild to severe disorders. Since the human body is not capable of synthesizing most of the essential micronutrients, the only way to obtain them is through dietary food sources or through supplementation.

The principal micronutrients fall into two categories—vitamins and minerals. Vitamins are essential micronutrients that the body is not capable of synthesizing in sufficient quantities for its growth and maintenance and have to be derived from dietary food sources. However, most vitamins are present only in minute quantities in the foods that we ingest and their bioavailability depends on the food source. There are thirteen essential vitamins of which four, A, D, E, and K are fat soluble and nine, B1, B2, B3, B6, B12, pantothenic acid, biotin, folic acid, and C are water soluble. The fat soluble vitamins are capable of being retained in the body while the water soluble vitamins are excreted from the body.

Minerals which form the second category of micronutrients are inorganic in nature and can be broken down into two sub-categories: macrominerals such as calcium (Ca), phosphorous (P), sodium (Na), potassium (K), magnesium (Mg), and chloride (Cl) and trace minerals such as iron (Fe), zinc (Zn), iodine (Io), selenium (Se), copper (Cu), manganese (Mn), fluoride (fl), chromium (Cr) and molybdenum (Mo). Just as with the essential vitamins, these mineral micronutrients are essential for bodily functions and cannot be synthesized by the body. Therefore, it is necessary to have an adequate intake of these mineral micronutrients from food sources or through supplementation.

Several micronutrients including zinc, iron and vitamin A have been shown to play a critical role in normal growth. The most conclusive evidence to date linking the intake of a specific micronutrient to child growth is for zinc, though the mechanisms by which zinc deficiency impairs growth has not been elucidated. Iron deficiency is associated with anemia and impaired physical growth (Owen G M et al, 1971. Journal of Pediatrics 79:563-568; Rao et al., 1980. Indian J Med Res 71:237-426), but iron supplement alone had no significant effect on child growth (e.g. Ramakrishnan U et al. 2004. Journal of Nutrition 134:2592-2602). Several observational studies reported significant correlations between vitamin A status and stunting (Fawzi W W et al, 1997. Epidemiology 8: 402-407; Kurugol Z et al., 2000. Epidemiology 14:64-69). However, a later Meta analysis by Ramakrishnan et al. (2004, ibid) concluded that vitamin A supplementation interventions had no significant effect on growth.

It has been shown that arginine and lysine, when taken together orally, can increase the release of the body's own stored, natural growth hormone (Isidori A et al. 1981. Current Medical Research and Opinion 7(7):475-481). The effect appeared to be specific to the combination of the two amino acids; neither of the amino acids demonstrated appreciable stimulating activity when administered alone. U.S. Pat. No. 6,346,264 discloses a nutritional supplement for ingestion by humans for restoring growth hormone levels consisting of combinations of amino acids selected from branched chain amino acids chosen from the group leucine, isoleucine, and valine; together with free form amino acids chosen from the group lysine, glutamine, ornithine, arginine, and glycine.

U.S. Patent Application Publication No. 2007/0037861 discloses the use of combination therapy comprising growth hormone (GH) and at least one free fatty acid (FFA) regulator in the treatment of conditions that require or have the potential to require treatment with GH.

Most of the studies which explored the role of specific nutrients in growth and the effect of supplements enriched with these nutrients have focused on malnourished children populations in developing countries (for example, Allen L H et al. 1992. Am J Clin Nutr 56:353-364; Abrams S A et al. 2003. Journal of Nutrition 133:1834-1840).

The effect of a commercially available nutritional composition (PediaSure®) on weight-for-height measurements have been examined in children age 3-5 years with picky-eater behaviors in the Philippines and Taiwan. The supplement, designed to provide complete balanced nutrition for children 1-6 years old and containing 25 vitamins and minerals was given in addition to nutritional counseling, and was shown to enhance both weight and height compared to nutritional counseling alone (Alarcon P A et al. 2003. Clin Pediat 42:209-217). However, the starting point of the participating children was relatively high (below the 25$^{th}$ percentile in weight-for height) and the study ended after 90 days.

Few studies which explored the relations between nutrition and growth were performed in developed countries, where food is not limited. These studies focused on short stature children with idiopathic etiology. These children are often characterized as poor eaters and having a lean body (Wudy S A et al., 2005. Pediatrics 116(1), e52-e57; Thibault H et al., 1993. Horm Res 40 (4):136-140).

Several approaches have been taken for the development of nutritional supplements that can promote healthy development and growth. For example, U.S. Pat. No. 8,287,932 discloses nutritional composition including a lipid or fat; a protein source; at least about 5 mg/100 kcal of a source of long chain polyunsaturated fatty acids which comprises docosahexanoic acid; and at least about 0.2 mg/100 kcal of a prebiotic composition, wherein the prebiotic composition comprises a plurality of oligosaccharides such that the overall fermentation rate profile of the prebiotic composition provides an increased population of beneficial bacteria in the human gut over an extended period of time.

U.S. Patent Application Publication No. 2013/0017182 discloses dietary micronutrient supplement formulations for specific ages, gender, special requirements and health conditions comprising, vitamins, minerals, fish and plant oils, amino acids, enzymes, phytochemicals, herb and fruit extracts and other natural compounds grouped into morning, mid-day and evening formulas based on their synergism and antagonism with each other, their interactions with ingredients in the food consumed during each meal and their bioavailability. The dietary micronutrient formulations are optimized to meet the Recommended Daily Allowances (RDA) and Adequate Intake (AI) standards for each segment of the population with larger amounts of nutrients used in condition-specific formulas.

There is an unmet need for, and would be highly advantageous to have a nutritional supplement specifically designed to enhance the linear growth of pre-pubertal children who are significantly shorter than the norm.

SUMMARY OF THE INVENTION

The present invention provides nutritional supplements specifically designed to improve the growth, particularly the linear growth, of pre-pubertal children who are significantly short compared to the norm, including healthy pre-pubertal children. The nutritional supplements of the invention provide at least one measure of improved growth selected from an enhancement in growth rate; maintenance of normal growth rate and elevating the final stature of a human subject.

The present invention is based in part on the unexpected discovery that a nutritional supplement comprising an energy source and a particular combination of macro- and micro-nutrients, including arginine, is significantly effective in enhancing the linear growth of pre-pubertal children that were below the $10^{th}$ percentile in terms of height and weight when intervention was initiated.

Without wishing to be bound by any particular theory or mechanism of action, the efficacy of the nutritional supplement of the invention may be attributed to the specific composition and ratios of the micronutrients within the nutritional supplement formula resulting in optimal absorption and synergistic activity. According to the principles of the present invention the micronutrients, together with a highly balanced energy source and the amino acid arginine provide for the growth stimulation. According to some embodiments the only free amino acid added to the supplement is arginine.

Moreover, the present invention discloses for the first time that children who consumed at least 2.5 g per kg body weight per day of the supplement of the invention improved their height-standard deviation score (height-SDS) 2.5 times more compared to children not consuming the supplement. This improvement was observed even after only six months of intervention. This increase is significantly higher compared to the height improvement observed with hitherto known nutritional supplements.

Thus, according to one aspect, the present invention provides a nutritional supplement in powder form having per 100 g powder a total caloric content of from about 300 kcal to about 500 kcal comprising per 100 g powder arginine in an amount of from about 250 mg to about 1000 mg and a micronutrient combination comprising calcium in an amount of from about 250 mg to about 750 mg; vitamin C in an amount of from about 15 mg to about 350 mg; zinc in an amount of from about 2.0 mg to about 15 mg; iron in an amount of from about 2.0 mg to about 10 mg; vitamin A in an amount of from about 50 µg to about 350 µg; and vitamin D in an amount of from about 2 µg to about 10 µg.

According to certain embodiments, 40% to 70% of the total caloric content of the supplement is carbohydrates. According to other embodiments, 10% to 40% of the total caloric content is lipids. According to yet additional embodiments, 10% to 40% of the total caloric content is proteins. According to certain exemplary embodiments, the total caloric content comprises 40% to 70% carbohydrate, 10% to 40% lipids and 10% to 40% proteins.

According to certain exemplary embodiments, the carbohydrate component of the nutritional supplement comprises from 40% to 55% of the total caloric content of the supplement. According to yet other exemplary embodiments, the carbohydrate component of the nutritional supplement comprises about 48% of the total caloric content of the supplement.

According to additional exemplary embodiments, the lipid component of the nutritional supplement comprises from 20% to 30% of the total caloric content of the supplement. According to yet other exemplary embodiments, the lipid component of the nutritional supplement comprises about 25% of the total caloric content of the supplement.

According to further exemplary embodiments, the protein component of the nutritional supplement comprises from 20% to 35% of the total caloric content of the supplement. According to yet other exemplary embodiments, the protein component of the nutritional supplement comprises about 28% of the total caloric content of the supplement.

According to other embodiments, the nutritional supplement comprises per 100 g powder arginine in an amount of from about 500 mg to about 1000 mg; calcium in an amount of from about 300 mg to about 400 mg; vitamin C in an amount of from about 15 mg to about 50 mg; zinc in an amount of from about 2.0 mg to about 5.0 mg; iron in an amount of from about 3.0 mg to about 5.0 mg; vitamin A in an amount of from about 50 µg to about 150 µg; and vitamin D in an amount of from about 2 µg to about 3.5 µg.

According to certain exemplary embodiments, the nutritional supplement has total caloric content of about 418 kcal/100 g powder, comprising per 100 g powder arginine in an amount of about 826-992 mg; calcium in an amount of about 413 mg; vitamin C in an amount of about 24-28 mg; zinc in an amount of about 4.0 mg; iron in an amount of about 4.5 mg; vitamin A in an amount of about 118-142 µg; and vitamin D in an amount of about 3.0-3.5 µg.

According to certain embodiments, the nutritional supplement of the invention is for enhancing the linear growth of pre-pubertal human subjects. According to these embodiments, the pre-pubertal human subjects are short and lean 3-9 years old children.

The nutritional supplement of the invention can be formulated in any suitable form as is known to a person skilled in the art. According to certain exemplary embodiments, the nutritional supplement is in a powder form for dilution with water or other beverage before use.

According to other embodiments, the nutritional supplement of the invention is formulated as a ready-to-use composition. The ready to use composition can be in the form of a liquid, paste, pudding, solid bar and the like.

The vitamins, minerals, proteins, lipids and carbohydrates included in the nutritional supplements of the invention can be used in any suitable form for producing the nutritional powder or ready-to-use formula of the invention. According to certain embodiments, the vitamin and minerals are provided in a bio-available form. According to certain exemplary embodiments, the vitamin and minerals are provided in their most bio-available form.

According to yet another aspect, the present invention provides a method for improving the growth of a pre-pubertal human subject, comprising administering to a pre-pubertal human subject having a short stature compared to the norm a nutritional composition according to the teachings of the present invention, thereby improving the growth of the pre-pubertal human subject.

According to certain exemplary embodiments, the term "short stature compared to the norm" refers to a pre-pubertal subject height below the $10^{th}$ percentile. According to additional embodiments, the subject weight is also below the $10^{th}$ percentile.

According to certain embodiments, the pre-pubertal human subject is at age 3-9. According to other embodiments the pre-pubertal human subject is healthy. According to yet additional embodiments, the pre-pubertal human subject has normal levels of growth hormone.

According to other embodiments, the method results in enhancing the growth rate of said subject. According to these embodiments, the growth rate is enhanced by additional 0.5-3.0 cm per year relative to the expected growth rate.

According to additional embodiments, the method results in elevating the final stature measure of said subject relative to the expected measure. According to some embodiments, the final stature measure is elevated by 0.5 cm to 5 cm.

According to yet additional embodiments, the method is for maintaining the growth rate of said subject.

According to certain embodiments, the nutritional supplement of the invention is administered at an amount of at least 1 g/kg BW/day. According to some embodiments, the body weight is the weight measured when intervention was initiated. According to other embodiments, the supplement is administered at an amount of between 1.25 to 5.5 g per kg BW/day.

There is no significance to the number of portions of the nutritional supplement consumed as long as the minimal total effective amount is consumed. According to certain exemplary embodiments, the nutritional supplement is administered once daily.

According to a further aspect, the present invention provides a nutritional supplement, said supplement containing total caloric content of from about 300 kcal to about 500 kcal and a micronutrient composition comprising per 100 g powder arginine in an amount of from about 250 mg to about 1000 mg; calcium in an amount of from about 250 mg to about 750 mg; vitamin C in an amount of from about 15 mg to about 350 mg; zinc in an amount of from about 2.0 mg to about 15 mg; iron in an amount of from about 2.0 mg to about 10 mg; vitamin A in an amount of from about 50 µg to about 350 µg; and vitamin D in an amount of from about 2 µg to about 10 µg, for use in improving the growth of pre-pubertal human subject.

Other objects, features and advantages of the present invention will become clear from the following description and drawings.

DETAILED DESCRIPTION OF THE INVENTION

The present invention provides nutritional supplement tailored to meet the need to improve the growth, particularly the linear growth of pre-pubertal human subjects with short stature and typically lean body structure.

The nutritional composition of the present invention is so designed as to provide adequate amounts and combination of micronutrients and macronutrient along with optimized energy content. Moreover, the composition of the various ingredients within the nutritional supplement has been planned to ensure optimal absorption of each and every element in its bio-active form providing maximal activity within the human body.

As used herein the terms "improved growth" or "improving the growth" relate to an enhancement in growth rate; maintenance of normal growth rate and elevating the final stature measure of a human subject.

The terms "micronutrient" or "micronutrients" are used herein in their broadest scope as is known to a person skilled in the art. Micronutrients are nutrients required by humans and other organisms throughout life in small quantities to orchestrate a range of physiological functions.

According to certain aspects of the invention, the nutritional supplement is in a powder form comprising per 100 g powder a total caloric content of from about 300 kcal to about 500 kcal and arginine in an amount of from about 250 mg to about 1000 mg. According to some embodiments, the arginine content is from about 500 mg to about 1000 mg. According to certain exemplary embodiments, the arginine content is about 800-1000 mg/100 g powder.

As used herein, the term "about" refers to the designated measure ±10%. For example, about 300 kcal should mean from 270 to 330 kcal.

Arginine (abbreviated as Arg or R) is an α-amino acid. It was first isolated in 1886. The L-form is one of the 20 most common natural amino acids. Arginine is a conditionally nonessential amino acid, i.e. it can be manufactured by the human body, but the biosynthetic pathway does not produce all the arginine amounts required for normal body function, such that additional amounts must be consumed through the diet. Individuals with poor nutrition or certain physical conditions typically do not have sufficient internally synthesized arginine and are advised to increase their intake of foods containing arginine. Arginine is found in a wide variety of foods, including from animal and plant sources. Arginine has been reported to play a role in the secretion of growth hormone, particularly in increasing the level of growth hormone in resting subjects taking arginine orally. However, other studies did not confirm these finding. In all cases, the studies were performed with adult human subjects. As exemplified hereinbelow, the present invention now shows that a nutritional supplement comprising arginine at a high quantity ratio compared to the additional micronutrients present in the supplement formula significantly enhanced the liner growth of pre-pubertal short to the norm lean human subjects.

It is to be explicitly understood that the term "arginine" as used herein refers to any form of the amino acid known in the art, particularly any form known to be used as a nutritional supplement, including, but not limited to, the free amino acid; salts thereof, including, for example, arginine hydrochloride; decarboxylated arginine; di- or tri-arginine peptides and the like.

According to one aspect, the present invention provides a nutritional supplement in a powder form having per 100 g powder a total caloric content of from about 300 kcal to about 500 kcal comprising per 100 g powder arginine in an amount of from about 250 mg to about 1000 mg and a micronutrient composition comprising calcium in an amount of from about 250 mg to about 750 mg; vitamin C in an amount of from about 15 mg to about 350 mg; zinc in an amount of from about 2.0 mg to about 15 mg; iron in an amount of from about 2.0 mg to about 10 mg; vitamin A in an amount of from about 50 µg to about 350 µg; and vitamin D in an amount of from about 2 µg to about 10 µg.

According to some embodiments, the nutritional supplement of the present invention does not contain additional amino acids other than arginine.

According to one embodiment, the micronutrient composition consists of calcium in an amount of from about 250 mg to about 750 mg; vitamin C in an amount of from about 15 mg to about 350 mg; zinc in an amount of from about 2.0 mg to about 15 mg; iron in an amount of from about 2.0 mg to about 10 mg; vitamin A in an amount of from about 50 µg to about 350 µg; and vitamin D in an amount of from about 2 µg to about 10 µg per 100 g powder.

Several micronutrients, including zinc, iron and vitamin A have been previously reported to play a role in normal growth of the human body.

Zinc is an essential mineral that is naturally present in some foods. Several hundred zinc-containing nucleoproteins are involved in gene expression of multiple proteins, many of which are important for growth. Moreover, zinc deficiency reduces the production of insulin-like growth factor-1 (IGF-1) and may decrease cellular IGF responsiveness (Cole C R and Lifshitz E., 2008. Pediatric Endocrinol Rev 5(4): 889-96). Multiple studies have been carried out to assess the effect of zinc supplementation on children's growth. A mete-analyses of 33 randomized controlled intervention trials revealed that zinc supplementation produced significant positive responses in height and in weight increments (Brown K H et al., 2002. Am J Clin Nutr 75:1062-71). Some later studies based on children populations with zinc deficiency showed similar results, where zinc supplementations increased height and weight percentile (Hakimi S M et al., 2006. Arch Iran Med 9(2):148-52; Gibson et al, 2007. Br J Nutr 97(1):167-75). In children with idiopathic short stature with normal serum zinc levels, zinc supplementation increased basal IGF-I, IGFBP-3, alkaline phosphatase and osteocalcin without changing growth hormone response to clonidine. Despite improvement in the above parameters, zinc supplementation did not significantly changed height or weight-SDS during 6-12 months follow-up period. Zinc supplementation did not affect sensitivity to exogenous growth hormone as tested by IGF-I and IGFBP-3 generation test (Imamoglu S et al., 2005. J Pediatr Endocrinol Metab 18(1): 69-74).

Several observational studies have documented a relationship between iron-deficiency anemia and impaired physical growth (Owen et al, 1971; Rao et al., 1980, ibid). The proposed mechanisms through which iron deficiency may impair growth include its effects on immunity, appetite, thermogenesis and thyroid hormone metabolism (for example, Lawless J W et al., 1994. J Nutr. 124(5):645-54.). A Meta analysis by Ramakrishnan et al. (2004, ibid) found that although iron interventions resulted in a significant increase in hemoglobin concentrations with an effect size of 1.49 (95% CI: 0.46, 2.51), there was no significant effect of iron supplementation intervention on child growth. Similar results and conclusions were made by a later systematic review of randomized controlled trials by Sachdev H P S et al. (2006. Public health Nutrition 9(7):904-20). where the pooled estimates did not document a statistical significant positive effect of iron supplementation on any anthropometric variable (weight for age, weight for height, height for age). It is important to note that most of the studies included in the Meta analysis of Ramakrishnan et al. (2004, ibid) and the systematic review of Sachdev et al. (2006, ibid) were from developing countries, where food supply is limited. In such conditions, even improvement in the child's appetite may not translate into increased energy intake, and therefore enhanced linear growth. Beckett et al. documented a significant increase in physical growth in undernourished Indonesian children with combination of energy and iron supplementation, but this finding needs further validation (Beckett C et al. 2000. Eur J Clin Nutr. 54 Suppl 2:S52-59).

Significant correlations between vitamin A status and stunting have been found in several observational studies (Fawzi et al., 1997, ibid; Fuchs G J et al. 1994. Am J Clin Nutr 60: 293-298; Kurugol et al, 2000, ibid). The results from randomized controlled trials (RCTs), however, are contradictory (Ramakrishnan et al. 2004, ibid). In a review by Bhandari et al., the authors concluded that routine vitamin A supplementation has little or no impact on linear growth, and that more research is needed to allow any conclusion on the impact of vitamin A in children with deficiency in this vitamin (Bhandari N et al., 2001. Br J Nutr 85(suppl 2): S131-S137). A later Meta analysis by Ramakrishnan et al (2004, ibid) concluded that vitamin A supplementation interventions had no significant effect on growth.

The particular combination of micronutrients provided in a nutritional composition is of significance in exerting each of the micronutrient activity. Few RCTs examined the effect of zinc-iron supplementation on linear growth of stunted children. Perrone et al. evaluated the effect of one year supplementation of iron plus zinc, zinc alone and placebo on growth (Perrone L et al., 1999. J Trace Elem Med Biol 1999; 13(1-2):51-56). Before supplementation, serum and erythrocyte ferritin and hair zinc contents were significantly lower in the short study group compared to age-matched control subjects. Iron plus zinc supplementation caused an improvement in growth rate in all subjects. In the zinc-supplemented group, only children whose ferritin levels were higher than 20 ng/L before supplementation showed a similar improvement of growth rate. Similar benefit to the combination of zinc and iron supplementation was found in a later large double-blind intervention study by Fahmida et al. (Fahmida U et al., 2007. Asia Pac J Clin Nutr 2007; 16(2): 301-309). This study involved 800 infants 3-6 month from west Tenggara. Syrup consists of zinc alone, zinc+iron, zinc+iron+vitamin A or placebo, were given daily for six months. The results showed a positive effect on linear growth among initially stunted infants in the zinc+iron, zinc+iron+vitamin A groups who grew 1.1-1.5 cm longer then placebo. In the zinc-alone group, mean height for age Z-score decreased to a greater extent than placebo. The authors attribute this finding to the low iron status of the subjects, and comment that zinc supplementation would have positive effect on growth if the low iron status is also corrected (Fahmida et al, 2007, ibid). On the other hand, in the study of Rosado et al. (1997) no differences in linear growth were observed between Mexican children supplemented with zinc and iron as compared to children receiving placebo for one year (Rosado J L et al., 1997. Am J Clin Nut 65:13-19). The investigators attributed the lack of impact to concurrent deficiencies of other micronutrients. In a later study of Rosado et al (Rosado J L et al., 1999. J of Nut 129:531S-533S), when mixture of micronutrients was given as a supplement to children over a period of one year, a small significant impact on linear growth was found (effect size 0.14 SD units), and a greater benefit was observed in children receiving the supplement that belonged to the low and medium socio-economic status.

In addition to supplying a combination of micronutrients, the composition of the present invention further supplies energy. Without wishing to be bound by a specific theory or mechanism of action, this combination may provide for the significant effect of the nutritional supplement of the invention on the linear growth of pre-pubertal children.

According to certain embodiments, 40% to 70% of the total caloric content of the supplement is carbohydrates. According to other embodiments, 10% to 40% of the total caloric content is lipids. According to yet additional embodiments, 10% to 40% of the total caloric content is proteins. Each possibility represents a separate embodiment of the invention.

According to certain exemplary embodiments, the carbohydrate component of the nutritional supplement comprises from 40% to 55% of the total caloric content of the supplement. According to yet other exemplary embodiments, the carbohydrate component of the nutritional supplement comprises about 48% of the total caloric content of the supplement.

Any carbohydrate conventionally used in nutritional compositions is useful in the composition of the supplement of this invention. According to certain exemplary embodiments, carbohydrate component is selected from the group consisting of, but not limited to sucrose, modified starch, nutritional fibers and combinations thereof.

According to additional exemplary embodiments, the lipid component of the nutritional supplement comprises from 20% to 30% of the total caloric content of the supplement. According to yet other exemplary embodiments, the lipid component of the nutritional supplement comprises 25% of the total caloric content of the supplement.

Adequate lipid intake is important as a source of energy and essential fatty acids and as a carrier of fat soluble vitamins. Suitable lipids for use according to the teachings of the present invention include any of the conventional saturated and unsaturated fatty acids, glycerides and other nutritionally acceptable fat sources known in the art, such fat sources include animal oils, fish oils, vegetable oils and synthetic lipids. According to certain exemplary embodiments, the lipid component of the nutritional supplement consists essentially of canola oil.

According to further exemplary embodiments, the protein component of the nutritional supplement comprises from 20% to 32% of the total caloric content of the supplement. According to yet other exemplary embodiments, the protein component of the nutritional supplement comprises about 28% of the total caloric content of the supplement.

According to certain exemplary embodiments the protein component is selected from the group consisting of, but not limited to, whey protein, low fat milk powder and combination thereof.

According to some embodiments, the nutritional supplement of the invention consists of carbohydrates, lipid and proteins providing a total caloric content per 100 g powder of from about 300 kcal to about 500 kcal, consisting of per 100 g powder arginine in an amount of from about 250 mg to about 1000 mg calcium in an amount of from about 250 mg to about 750 mg; vitamin C in an amount of from about 15 mg to about 350 mg; zinc in an amount of from about 2.0 mg to about 15 mg; iron in an amount of from about 2.0 mg to about 10 mg; vitamin A in an amount of from about 50 µg to about 350 µg; and vitamin D in an amount of from about 2 µg to about 10 µg.

The nutritional compositions of the invention may provide minimal, partial, or total nutritional support. In preferred exemplary embodiments, the supplement is administered in conjunction with a food or other nutritional composition. In these embodiments, the compositions can either be intermixed with the food or other nutritional compositions prior to ingestion by the subject or can be administered to the subject either before or after ingestion of the food or other nutritional composition.

The supplement may, but need not, be nutritionally complete. The skilled Artisan will recognize "nutritionally complete" to vary depending on a number of factors including, but not limited to, age, clinical condition, and dietary intake of the subject to whom the term is being applied. In general, "nutritionally complete" means that the nutritional supplement of the present invention provides adequate amounts of all carbohydrates, lipids, essential fatty acids, proteins, essential amino acids, conditionally essential amino acids, vitamins, minerals, and energy required for normal growth. As applied to nutrients, the term "essential" refers to any nutrient which cannot be synthesized by the body in amounts sufficient for normal growth and to maintain health and which therefore must be supplied by the diet. The term "conditionally essential" as applied to nutrients means that the nutrient must be supplied by the diet under conditions when adequate amounts of the precursor compound is unavailable to the body for endogenous synthesis to occur.

The nutritional supplement may be provided in any form known in the art, including a powder, a suspension, a paste, a pudding, a solid, a liquid, a liquid concentrate, or a ready-to-use product. According to certain exemplary embodiment, the nutritional supplement is in a form of a powder.

As used herein, the term "powder" refers to any form of dry material. For powder embodiments of the present invention, such powders are typically in the form of flowable or substantially flowable particulate compositions or at least particulate compositions that can be easily scooped and measured with a spoon or similar other device, wherein the compositions can easily be reconstituted by the intended user with a suitable aqueous fluid, typically water, to form a liquid nutritional formula for immediate oral use. In this context, "immediate" use generally means within about 48 hours, typically within about 24 hours, most typically right after reconstitution. These powder embodiments include spray dried, agglomerated, dry mixed or other known or otherwise effective particulate form.

The quantity of a nutritional powder required to produce a volume suitable for one serving can vary. According to certain exemplary embodiments, the quantity of one serving is 80-90 g powder, typically 84.7 g powder. One powder serving of the nutritional supplement of the invention can be reconstituted in variable volumes of liquid or other excipients. According to certain exemplary embodiments, one powder serving is dissolved in 200 ml of liquid. According certain embodiments, the liquid is water. According to other embodiments, the liquid is a beverage other than water.

The nutritional supplement of the present invention may be packaged and sealed in single dosage forms or in multi-use containers. When in a powder form the sealed package can be stored under ambient conditions. Single dosage form is, in one embodiment, a package comprising powder in an amount for one serving to be dissolved in an excipient, typically water or another beverage. In another embodiment a single dosage form is a ready-to-use formula containing one serving of the nutritional supplement. For multi-use containers, the package can be opened and then covered for repeated use by the ultimate user, provided that the covered package is then stored under ambient conditions (e.g., avoid extreme temperatures) and the contents used within about one month or so.

According to yet another aspect, the present invention provides a method for improving the growth of a pre-pubertal human subject, comprising administering to a pre-pubertal human subject having a short stature compared to the norm a nutritional supplement thereby improving the growth of the pre-pubertal human subject, wherein the nutritional supplement has total caloric content of from about 300 kcal to about 500 kcal, comprising arginine in an amount of from about 250 mg to about 1000 mg and a micronutrient combination comprising calcium in an amount of from about 250 mg to about 750 mg; vitamin C in an amount of from about 15 mg to about 350 mg; zinc in an amount of from about 2.0 mg to about 15 mg; iron in an amount of from about 2.0 mg to about 10 mg; vitamin A in an amount of from about 50 µg to about 350 µg; and vitamin D in an amount of from about 2 µg to about 10 µg.

According to some embodiments, the nutritional supplement comprises arginine in an amount of from about 500 mg to about 1000 mg; calcium in an amount of from about 300 mg to about 400 mg; vitamin C in an amount of from about 15 mg to about 50 mg; zinc in an amount of from about 2.0 mg to about 5.0 mg; iron in an amount of from about 3.0 mg to about 5.0 mg; vitamin A in an amount of from about 50 µg to about 150 µg; and vitamin D in an amount of from about 2 µg to about 3.5 µg.

According to certain exemplary embodiments, the nutritional supplement has a total caloric content of about 418 kcal, arginine in an amount of about 826-992 mg; calcium in an amount of about 413 mg; vitamin C in an amount of about 24-28 mg; zinc in an amount of about 4.0 mg; iron in an amount of about 4.5 mg; vitamin A in an amount of about 118-142 µg; and vitamin D in an amount of about 3.0-3.5 µg.

According to certain exemplary embodiments, the term "short stature compared to the norm" refers to a pre-pubertal subject height below the $10^{th}$ percentile. According to additional embodiments, the subject weight and BMI are also below the $10^{th}$ percentile.

According to certain embodiments, the pre-pubertal human subject is at age 3-9. According to other embodiments the pre-pubertal human subject is healthy. According to yet additional embodiments, the pre-pubertal human subject has normal levels of growth hormone.

According to other embodiments, the method is for enhancing the growth rate of said subject. According to these embodiments, the growth rate in enhanced by additional 0.5-3.0 cm per year relative to the expected growth rate.

The enhancement of the growth rate during time can be constant or variable. It is to be explicitly understood that enhancement of a growth rate includes catch up growth. As used herein, the term "catch up growth" refers to height velocity above the statistical limits of normality for age and/or maturity during a defined period of time, after a transient period of growth inhibition.

According to additional embodiments, the method is for elevating the final stature measure of said subject relative to the expected measure. According to these embodiments, the final stature measure is elevated by 0.5 cm to 5 cm.

According to yet additional embodiments, the method is for maintaining the growth rate of said subject. According to these embodiments, the nutritional supplement of the invention provides for a growth rate that is similar to the growth rate of a healthy subject of the same gender and age.

According to certain embodiments, the nutritional supplement of the invention is administered at an amount of at least 1 g/kg BW at base-line/day. According to other embodiments, the supplement is administered at an amount of between 1.25 to 5.5 g/kg base-ine BW/day.

There is no significance to the number of portions of the nutritional supplement consumed as long as the minimal total effective amount is consumed. According to certain exemplary embodiments, the nutritional supplement is administered once a day.

According to certain exemplary embodiments, the nutritional supplement is administered once daily for a duration of at least 6 months. According to other embodiments, the nutritional supplement is administered once daily for a duration of at least 7 month, 8 months, 9 months, 10 months, 11 months or 12 months. Each possibility represents a separate embodiment of the present invention. According to certain exemplary embodiments, the nutritional supplement is administered daily for duration of at least 12 months.

According to a further aspect, the present invention provides a nutritional supplement, said supplement having per 100 g powder a total caloric content of from about 300 kcal to about 500 kcal comprising per 100 g powder arginine in an amount of from about 250 mg to about 1000 mg and a micronutrient composition comprising calcium in an amount of from about 250 mg to about 750 mg; vitamin C in an amount of from about 15 mg to about 350 mg; zinc in an amount of from about 2.0 mg to about 15 mg; iron in an amount of from about 2.0 mg to about 10 mg; vitamin A in an amount of from about 50 µg to about 350 µg; and vitamin D in an amount of from about 2 µg to about 10 µg for use in improving the growth of pre-pubertal human subject.

According to certain embodiments, the nutritional supplement is for use in improving the growth of pre-pubertal human subject age 3-9. According to other embodiments, the human subject is healthy. According to other embodiments, the human subject has normal levels of growth hormone.

According to other embodiments, the nutritional supplement is for use in the growth rate of said subject. According to these embodiments, the growth rate in enhanced by additional 0.5-3.0 cm per year relative to the expected growth rate.

According to other embodiments, the nutritional supplement is for use in elevating the final stature measure of said subject relative to the expected measure. According to these embodiments, the final stature measure is elevated by 0.5 cm to 5 cm.

According to other embodiments, the nutritional supplement is for use in maintaining the growth rate of said subject.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Exemplary Formulation of the Nutritional Supplement

An exemplary formula of the nutritional supplement is presented in Table 1 hereinbelow.

TABLE 1

Exemplary Nutritional Supplement

| | Amount per Serving (84.7 g) | Amount per 100 g |
|---|---|---|
| Calories | 354 kcal | 418 kcal |
| Total carbohydrate | 42.4 g | 50 g |
| Total fat | 10.2 g | 12.0 g |
| Saturated fat | 1.5 g | 1.8 g |
| Protein | 24.5 g | 28.9 g |
| Sodium | 149 mg | 176 mg |
| Potassium | 192 mg | 227 mg |
| Phosphorus | 96 mg | 113 mg |
| Calcium | 350 mg | 413.2 mg |
| Vitamin D | 2.45-2.58 µg | 2.9-3.5 µg |
| Iron | 3.9 mg | 4.5 mg |
| Vitamin C | 20-24 mg | 23.6-28.3 mg |
| Vitamin A | 100-120 µg | 118.2-141.8 µg |
| Zinc | 3.2 mg | 3.7 mg |
| Arginine | 700-840 mg | 826.4-991.7 mg |

Example 2: Clinical Study: Effect of the Nutritional Composition on Linear Growth and Weight Gain Material and Methods A clinical study was designed for assessing the effect of the nutritional supplement of the invention on linear growth and weight gain of short and lean pre-pubertal (3-9 years old) children. The study was a 12-month double blind randomized controlled study (RCT). The study was conducted at the Institute for Endocrinology Schneider Children's Medical Center of Israel and received approval by the Institutional Review Board. Written informed consent from parents was sought prior to enrolment to the study.

Study Population

Eligible patients were healthy short and lean pre-pubertal children who were referred to the clinic for growth assessment.

Inclusion criteria were: age: girls 3-8 years; boys 3-9 years; height and weight $\leq 10^{th}$ percentile for age and gender; weight percentile≤height percentile; available velocity data for at least 4 months prior to study entry.

Recruitment aim was 200 participants (100 in each arm).

Exclusion criteria were: chronic and gastrointestinal disease including malabsorption; genetic syndromes; malignancy and any chronic medical treatment; intake of a medication that might adversely affect appetite, weight or growth.

Sample size was calculated based on the primary outcome of change in height standard deviation score (height-SDS) of 0.3, with an 80% chance of detecting a significant increase at the 2-sided 5% level, and included a 10% dropout rate.

Demographics and family medical history were collected at baseline by the study physician. Height and weight were expressed as SDS according to the recommendations of the Center for Disease Control and Prevention (Kuczmarski R J et al. 2000 CDC growth charts: United States. Adv Data 314:1-27). Body mass index (BMI) was calculated weight (kilograms)/height (meters squared), and expressed as BMI-SDS (Kuczmarski R J et al. 2000, ibid).

Study Design

The study includes two phases: phase 1 (0 to 6 months) blinded intervention with the study nutritional supplement formula or placebo; phase 2 (6 to 12 months) open extension with the test nutritional supplement. At the commencement of the study, the participants were randomly allocated to the test supplement or placebo in a 1:1 ratio. Phase 1 has been completed.

Participants were instructed to consume 1 sachet of the study formula or placebo (4 spoons of powder, total of about 85 g), mixed with 200 ml of water at dinner, in addition to their regular diet. Parents were asked to record the volume of nutritional supplement the child consumed each day. 'Good' consumption was defined as intake of 50% of the recommended dose and 'poor' consumption as intake of <50%.

Test Nutritional Supplement

The nutritional supplement formula used was standardized formula containing 25% of the recommended Dietary Reference Intake (DRI) for calories, high protein (28% of calories), vitamins and minerals (25%-100% of DRI for Recommended Daily Allowance (RDA) or adequate intake (AI). The placebo used was a low caloric, low protein formula, without added vitamins and minerals (the daily placebo portion contained total caloric content of 60 kcal, comprising 9.5 g carbohydrates, 3.3 g proteins and 1.1 g lipids)

Statistical Analysis

The data were analyzed using the SPSS software version 19 (SPSS, Inc., Chicago, Ill.). Analyses were performed on the basis of the intention-to-treat principle. Differences between intervention groups in continuous data were examined using independent-sample t tests (normally distributed data) or Mann-Whitney tests (skewed data). Chi-tests were used to examine the differences in categorical data. Comparisons between groups according to consumption category (good/poor) were done using one-way ANOVA. Post-hoc comparison analysis (Tukey) was used to detect differences between groups. Spearman's correlation was used to analyze correlations between the consumption (skewed data) and the increment in growth parameters and linear regression analysis for extrapolating the dose-response.

Results

Between November 2010 and November 2013, a total of 200 children (149 boys, 51 girls) entered the study and 171 (85.5%) completed the 6-month intervention (80 children of the group receiving the study formula and 91 of the placebo group) ($\chi 2=3.267$, df=1, p=0.071). The main reason for study withdrawal was refusal of the child to consume the supplement (15—study formula; 7—placebo). The median consumption rate significantly differed between the groups, with the group receiving the study formula having median consumption rate of 50% (interquartile range (IQR): 30%, 70%) and the group receiving the placebo having median consumption rate of 82.5% (IQR: 55%, 100%); p<0.001.

Table 2 presents the examined parameters of height (Ht-SDS), weight (Wt-SDS) and body-mass index (BMI-SDS) at baseline. No significant differences were observed in all the examined parameters between the group receiving the study formula and the group receiving placebo. Sub-categorization of the participants who completed the 6-month intervention according to consumption rate ("good"/"poor" as defined hereinabove) found no differences in their baseline anthropometric measurements.

TABLE 2

Base-line parameters

| | Study Formula (n = 100) | Placebo (n = 100) | P |
|---|---|---|---|
| Gender Boys/Girls | 76/24 | 73/27 | 0.626 |
| Age, years | 5.4 ± 1.5 | 5.6 ± 1.5 | 0.477 |
| Height-SDS | −2.04 ± 0.47 | −2.04 ± 0.43 | 0.962 |

TABLE 2-continued

Base-line parameters

|  | Study Formula (n = 100) | Placebo (n = 100) | P |
|---|---|---|---|
| Weight-SDS | −2.55 ± 0.58 | −2.57 ± 0.69 | 0.877 |
| BMI-SDS | −1.51 ± 0.64 | −1.58 ± 0.89 | 0.495 |

Data are presented as mean ± SD;
SDS—Standard Deviation Score

Changes in growth parameters after 6 months of intervention (study formula or placebo) are presented in Table 3. Children characterized as "good" consumers retained participation throughout the duration of the study whilst children characterized as "poor" consumers were more likely to withdraw from the study (p<0.001). "Good" consumers that received the study formula showed significant improvement in height-SDS (p<0.001) and weight-SDS (p=0.005) with no change in BMI-SDS as compared to "poor" consumers and the group receiving placebo. In the group treated with the study formula a positive correlation was found between the amount of formula consumed per body weight and the increment in Height-SDS and Weight-SDS (r=0.44, p<0.001 and r=0.35, p=0.002, respectively) but not with the increment in BMI-SDS (r=0.18, p=0.11). No significant correlations were found in the group receiving the placebo (Table 4). An average daily consumption of above 20 grams of the study formula (about 25% of the total daily amount of formula) or above 1.25 grams of the study formula per baseline body weight, resulted in improvement in both, height-SDS and weight-SDS, in a dose-response manner.

TABLE 3

Anthropometric changes after 6 months treatment with the study formula and placebo categorized by consumption category

| Consumption category | Study Formula | | Placebo | | P |
|---|---|---|---|---|---|
|  | "Poor" | "Good" | "Poor" | "Good" |  |
| Number (after 6 m/at baseline) | 37/57 | 43/43 | 18/27 | 73/73 | <0.001 |
| Δ Height-SDS | 0.00 ± 0.14$^a$ | 0.12 ± 0.12$^b$ | −0.02 ± 0.12$^a$ | 0.05 ± 0.16$^{ab}$ | <0.001 |
| Δ Weight-SDS | 0.02 ± 0.30$^a$ | 0.28 ± 0.35$^b$ | 0.06 ± 0.30$^a$ | 0.12 ± 0.35$^{ab}$ | 0.005 |
| Δ BMI-SDS | 0.08 ± 0.65 | 0.23 ± 0.47 | 0.09 ± 0.47 | 0.09 ± 0.59 | 0.559 |

P represents the difference among groups and consumption categories using one way ANOVA. Rates with different superscripts (a, b) differ significantly from each other in that row at p≤0.05; rates with no superscripts do no differ significantly from each other in that row (Post-hoc Tukey).

TABLE 4

Dose Response Analysis

|  | Study Formula | Placebo |
|---|---|---|
| Δ Height-SDS | r = 0.439 | r = 0.031 |
|  | p < 0.001 | p = 0.768 |
| Δ Weight-SDS | r = 0.347 | r = 0.148 |
|  | p = 0.002 | p = 0.161 |
| Δ BMI | r = 0.181 | r = 0.154 |
|  | p = 0.111 | p = 0.145 |

Some adverse events were reported during the study. Adverse events included gastrointestinal symptoms reported by 19 participants—7 of which received the study formula and 12 which received the placebo ($\chi 2$=1.071, df=1, p=0.301). One participant consuming the study formula developed pre-pubertal gynecomastia; thorough evaluation revealed no underlying endocrinopathy. Although this finding appears unrelated, the PI instructed the participant to discontinue formula consumption. No serious adverse events were reported during the study. As to infections, acute upper respiratory tract infections were reported by a total of 27 participants, 12 of which received the study formula group and 15 received the placebo (p=0.683). Acute gastrointestinal infections were reported by 14 participants, 2 who received the study formula and 12 who received the placebo group (p=0.008).

SUMMARY

After 6 months of the study, participants consuming the study formula had a significant improvement in both height and weight without developing obesity. The growth response to the study formula consumption was dose-dependent.

The effects of the nutritional supplement of the study were optimized in children who were adherent to therapy and consumed more than 50% of the recommended dose ("good" consumers). The average increase in height of participants categorized as "good" consumers was 0.12 SD (extrapolated one-year increment of 0.24 SD). This magnitude of improvement in height approaches the successful first year minimal response to growth hormone treatment (height SDS of 0.3) expected in idiopathic short stature (ISS) (Consensus ISS) (Cohen P et al. 2008. J Clin Endocrinol Metab. 93(11):4210-4217.

A positive impact of nutritional supplementation on the growth of children with picky eater behavior has been previously described (Alarcon et al., 2003, ibid; Ramakrishnan et al., 2004, ibid; Zadik et al., 2010. J Pediatr Endocrinol Metab 23(5):435-441). To the best ability of the inventors to ascertain, the nutritional supplement of the present invention is the first to combine an energy source, arginine and a particular combination of micronutrient. This nutritional supplement has been shown to significantly accelerate the growth rate of short, healthy children, particularly the linear growth. Of note, these studies were conducted in developing low income and low sanitation countries where children are considered as "nutritionally-at-risk" or malnourished (Sguassero Y et al. 2012. Cochrane Database Syst Rev. 6:CD005039.).

The main strength of the study present herein was the double-blinded, randomized, placebo controlled design of homogeneous population which allowed for causal relations between the intervention of nutritional supplement administration and outcomes to be established. Yet, the study has a limitation—the partial consumption of the recommended daily amount of the formula. The variety in the consumption rate enabled, however, to extrapolate the minimal dose (daily consumption of above 20 gr or 1.25 g/kg BW) required for growth promotion. The results presented herein show significant enhancement of the growth, particularly the linear growth. Thus, the particular combination of the nutritional supplement of the invention, even when consumed in a relatively small amounts, suffice to induce significant linear growth.

In conclusion, at least 6 months intervention with the innovative nutritional formula of the invention is safe and effective in promoting the physical growth of short and lean pre-pubertal children.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A nutritional supplement formulated in a powder form having per 100 g powder:
   a total caloric content of 418 kcal; arginine in an amount of from 826.4-991.7; calcium in an amount of 413.2 mg; vitamin C in an amount of from 23.6-28.3 mg; zinc in an amount of 3.7 mg; iron in an amount of 4.5 mg; vitamin A in an amount of from 118.2 µg to 141.8 µg; vitamin D in an amount of from 2.9 µg to 3.5 µg; total fat in an amount of 12.0 g; total carbohydrate in an amount of 50 g; and protein in an amount of 28.9 g;
   wherein the supplement is formulated in a dosage form selected from the group consisting of a sachet and a tablet, wherein the nutritional supplement increases linear growth without affecting body mass index (BMI) when administered to a pre-pubertal human subject at age 3-9.

2. The nutritional supplement of claim 1, wherein the dosage form is for dilution in water or another beverage.

3. The nutritional supplement of claim 1, said nutritional supplement is formulated as a ready-to-use supplement.

4. The nutritional supplement of claim 1, wherein the pre-pubertal human subject height is below the 10th percentile.

* * * * *